(12) United States Patent
McGrane et al.

(10) Patent No.: US 7,151,186 B2
(45) Date of Patent: Dec. 19, 2006

(54) METHOD FOR THE DIRECT ESTERIFICATION OF SORBITOL WITH FATTY ACIDS

(75) Inventors: Paul McGrane, Mountain View, CA (US); George W. Borden, Bat Cave, NC (US); Michael T. Wuesthoff, Gales Ferry, CT (US); Gary J. Flynn, Mystic, CT (US); James M. Anderson, Newmilford, CT (US); John Teixeira, Mystic, CT (US); Pankaj Shah, Lake Bluff, IL (US)

(73) Assignee: Danisco Cultor America, Inc., Ardsley, NY (US)

( * ) Notice: Subject to any disclaimer, the term of this patent is extended or adjusted under 35 U.S.C. 154(b) by 737 days.

(21) Appl. No.: 09/845,233

(22) Filed: Apr. 30, 2001

(65) Prior Publication Data

US 2002/0102340 A1 Aug. 1, 2002

Related U.S. Application Data

(63) Continuation of application No. 09/687,908, filed on Oct. 12, 2000, now abandoned.

(60) Provisional application No. 60/159,563, filed on Oct. 15, 1999.

(51) Int. Cl.
 *C11C 3/00* (2006.01)
(52) U.S. Cl. .................................. 554/167; 426/611
(58) Field of Classification Search ............. 554/167; 426/611
 See application file for complete search history.

(56) References Cited

U.S. PATENT DOCUMENTS

| 3,951,945 A * | 4/1976 | Heesen et al. ............ 536/18.2 |
| 4,334,061 A | 6/1982 | Bossier, III |
| 4,368,213 A | 1/1983 | Hollenbach et al. |
| 4,382,924 A | 5/1983 | Berling et al. |
| 4,461,782 A | 7/1984 | Robbins et al. |
| 4,517,360 A | 5/1985 | Volpenhein |
| 4,518,772 A | 5/1985 | Volpenhein |
| 4,562,007 A | 12/1985 | Stuehler |
| 4,611,055 A | 9/1986 | Yamamoto et al. |
| 4,705,690 A | 11/1987 | Brand et al. |
| 4,705,691 A | 11/1987 | Kupper et al. |
| 4,789,664 A | 12/1988 | Seligson et al. |
| 4,797,300 A | 1/1989 | Jandacek et al. |
| 4,806,632 A | 2/1989 | McCoy et al. |
| 4,810,516 A | 3/1989 | Kong-Chan |
| 4,822,875 A | 4/1989 | McCoy et al. |
| 4,835,001 A | 5/1989 | Mijae et al. |
| 4,877,871 A | 10/1989 | Klemann et al. |
| 4,880,657 A | 11/1989 | Guffey et al. |
| 4,883,684 A | 11/1989 | Yang |
| 4,919,964 A | 4/1990 | Adams et al. |
| 4,931,552 A | 6/1990 | Gibson et al. |
| 4,940,601 A | 7/1990 | Orphanos et al. |
| 4,942,228 A | 7/1990 | Gibson |
| 4,952,687 A | 8/1990 | Bodor et al. |
| 4,954,621 A | 9/1990 | Masaoka et al. |
| 4,960,602 A | 10/1990 | Talkington et al. |
| 4,962,092 A | 10/1990 | Wood, Jr. |
| 4,968,791 A | 11/1990 | Van Der Plank |
| 4,973,681 A | 11/1990 | Watanabe |
| 4,973,682 A | 11/1990 | Willemse |
| 5,006,360 A | 4/1991 | Howard et al. |
| 5,017,398 A | 5/1991 | Jandacek et al. |
| 5,021,256 A | 6/1991 | Guffey et al. |
| 5,039,544 A | 8/1991 | Lansbergen et al. |
| 5,043,438 A | 8/1991 | Buter |
| 5,055,571 A | 10/1991 | Van Lookeren |
| 5,061,503 A | 10/1991 | Kong-Chang et al. |
| 5,061,504 A | 10/1991 | Kong-Chang et al. |
| 5,064,677 A | 11/1991 | Cain et al. |
| 5,071,669 A | 12/1991 | Seiden |
| 5,079,355 A | 1/1992 | Meszaros Grechke et al. |
| 5,080,912 A | 1/1992 | Bodenstein et al. |
| 5,084,295 A | 1/1992 | Whelan et al. |
| 5,085,884 A | 2/1992 | Young et al. |
| 5,102,683 A | 4/1992 | Letton et al. |
| 5,124,301 A | 6/1992 | Wyness et al. |
| 5,130,151 A | 7/1992 | Averbach |
| 5,144,023 A | 9/1992 | Willemse |

(Continued)

FOREIGN PATENT DOCUMENTS

CA 1185610 6/1982

(Continued)

OTHER PUBLICATIONS

Giacometti et al. "Process for Preparing Nonionic Surfactant Sorbitan Fatty Acid Esters with and without Previous Sorbitol Cyclization" J. Argic. Food. Chem., vol. 44, 1996, pp. 3950-3954, XP002278710, Section Preparation of Esters.

(Continued)

*Primary Examiner*—Deborah D. Carr
(74) *Attorney, Agent, or Firm*—Knoble Yoshida & Dunleavy, LLC

(57) ABSTRACT

Mixtures of sorbitol fatty acid esters useful as low calorie fat substitutes are prepared through a direct esterification process. The process entails the direct esterification of sorbitol with free fatty acids, optionally in the presence of an esterification catalyst. The resulting sorbitol esters have an average degree of hydroxyl substitution ranging from about 3 to about 5.5. This partial esterification leads to a mixture of esters capable of serving as low calorie fat substitutes without undesirable physiological side effects or the need for additives. Furthermore, the direct esterification process proceeds without the need for large amounts of organic solvents or bleaching agents.

24 Claims, 1 Drawing Sheet

U.S. PATENT DOCUMENTS

| | | | |
|---|---|---|---|
| 5,147,675 A | 9/1992 | Gage et al. | |
| 5,158,796 A | 10/1992 | Bernhardt et al. | |
| 5,194,281 A | 3/1993 | Johnston et al. | |
| 5,211,979 A | 5/1993 | Bruijne et al. | |
| 5,225,049 A | 7/1993 | Barmentlo et al. | |
| 5,231,199 A | 7/1993 | Willemse | |
| 5,236,733 A | 8/1993 | Zimmerman et al. | |
| 5,239,097 A | 8/1993 | Barkey Wolf et al. | |
| 5,248,509 A | 9/1993 | Bruin | |
| 5,250,155 A | 10/1993 | Zwanenburg et al. | |
| 5,306,514 A | 4/1994 | Letton et al. | |
| 5,306,515 A | 4/1994 | Letton et al. | |
| 5,306,516 A | 4/1994 | Letton et al. | |
| 5,308,640 A | 5/1994 | Baer et al. | |
| 5,314,707 A | 5/1994 | Kester et al. | |
| 5,318,790 A | 6/1994 | Houston et al. | |
| 5,366,753 A | 11/1994 | Meyer et al. | |
| 5,370,892 A | 12/1994 | El-Nokaly et al. | |
| 5,378,478 A | 1/1995 | Miller et al. | |
| 5,419,925 A | 5/1995 | Seiden et al. | |
| 5,422,131 A | 6/1995 | Elsen et al. | |
| 5,440,027 A | 8/1995 | Hasenhuettl | |
| 5,451,416 A | 9/1995 | Johnston et al. | |
| 5,458,910 A * | 10/1995 | Gruetzmacher et al. | 426/611 |
| 5,472,728 A | 12/1995 | Miller et al. | |
| 5,474,795 A | 12/1995 | Surber et al. | |
| 5,480,667 A | 1/1996 | Corrigan et al. | |
| 5,486,372 A | 1/1996 | Martin et al. | |
| 5,491,226 A | 2/1996 | Kenneally | |
| 5,504,202 A | 4/1996 | Hutchinson | |
| 5,518,754 A | 5/1996 | Miller et al. | |
| 5,527,866 A | 6/1996 | Corrigan et al. | |
| 5,532,019 A | 7/1996 | Miller et al. | |
| 5,534,284 A | 7/1996 | Corrigan et al. | |
| 5,536,524 A | 7/1996 | Miller | |
| 5,559,226 A | 9/1996 | Sarama | |
| 5,580,966 A | 12/1996 | Buter et al. | |
| 5,587,196 A | 12/1996 | Mehnert et al. | |
| 5,596,085 A | 1/1997 | Silver et al. | |
| 5,648,483 A | 7/1997 | Granberg et al. | |
| 5,681,948 A | 10/1997 | Miller et al. | |
| 5,767,257 A | 6/1998 | Schafermeyer et al. | |

FOREIGN PATENT DOCUMENTS

| | | |
|---|---|---|
| CA | 2006132 | 12/1989 |
| EP | 0 233 856 A2 | 2/1987 |
| EP | 0 236 288 A2 | 2/1987 |
| EP | 0 236 288 B1 | 2/1987 |
| EP | 0 256 585 A1 | 7/1987 |
| EP | 0 256 585 B2 | 7/1987 |
| EP | 0256 585 B2 | 7/1987 |
| EP | 0 271 963 A2 | 12/1987 |
| EP | 0 271 963 A3 | 12/1987 |
| EP | 0 271 963 B1 | 12/1987 |
| EP | 0 311 154 A2 | 4/1988 |
| EP | 0 311 154 A3 | 4/1988 |
| EP | 0 311 154 B1 | 4/1988 |
| EP | 0 290 420 A2 | 5/1988 |
| EP | 0 290 420 A3 | 5/1988 |
| EP | 0 290 421 A2 | 5/1988 |
| EP | 0 290 421 A3 | 5/1988 |
| EP | 0 290 421 B1 | 5/1988 |
| EP | 0 354 600 A2 | 2/1989 |
| EP | 0 354 600 A3 | 2/1989 |
| EP | 0 354 600 B1 | 2/1989 |
| EP | 0 350 981 A1 | 6/1989 |
| EP | 0 350 981 B1 | 6/1989 |
| EP | 0 350 986 A1 | 6/1989 |
| EP | 0 350 986 B1 | 6/1989 |
| EP | 0 350 987 B1 | 6/1989 |
| EP | 0 350 988 A1 | 6/1989 |
| EP | 0 350 988 B2 | 6/1989 |
| EP | 0 350 987 A1 | 8/1989 |
| EP | 0 375 239 A2 | 12/1989 |
| EP | 0 375 239 B1 | 12/1989 |
| EP | 0 378 876 A3 | 12/1989 |
| EP | 0 378 876 B1 | 12/1989 |
| EP | 0 379 747 A2 | 12/1989 |
| EP | 0 379 747 A3 | 12/1989 |
| EP | 0 379 747 B1 | 12/1989 |
| EP | 0 387 876 A2 | 12/1989 |
| EP | 0 383 380 A2 | 2/1990 |
| EP | 0 383 380 A3 | 2/1990 |
| EP | 0 383 380 B1 | 2/1990 |
| EP | 0 384 508 A3 | 2/1990 |
| EP | 0 384 508 B1 | 2/1990 |
| EP | 0 .398 409 B1 | 3/1990 |
| EP | 0 398 409 A2 | 5/1990 |
| EP | 0 398 409 A3 | 5/1990 |
| EP | 0 416 665 A2 | 7/1990 |
| EP | 0 416 665 A3 | 7/1990 |
| EP | 0 416 665 B1 | 7/1990 |
| EP | 0 424 066 A2 | 10/1990 |
| EP | 0 424 066 A3 | 10/1990 |
| EP | 0 424 066 B1 | 10/1990 |
| EP | 0 548 272 B1 | 8/1991 |
| EP | 0 550 526 B1 | 8/1991 |
| EP | 0 615 972 A1 | 3/1993 |
| EP | 0 666 713 B2 | 10/1993 |
| EP | 0 233 856 B1 | 1/1994 |
| EP | 0 290 420 B1 | 1/1994 |
| EP | 0 757 031 | 2/1997 |
| GB | 2 282 313 | 4/1995 |
| JP | 5-125389 | 5/1993 |
| KR | 9108734 | 10/1991 |
| KR | 9210520 | 12/1992 |
| KR | 9303497 | 5/1993 |
| WO | WO 92/04360 | 3/1992 |
| WO | WO 92/04361 | 3/1992 |
| WO | WO 92/10941 | 7/1992 |
| WO | WO 93/19077 | 9/1993 |
| WO | WO 93/22932 | 11/1993 |
| WO | WO 94/09637 | 5/1994 |
| WO | WO 94/09640 | 5/1994 |
| WO | WO 97/00618 | 1/1997 |
| WO | WO 98/03525 | 1/1998 |
| WO | WO 98/03527 | 1/1998 |
| WO | WO 98/06731 | 2/1998 |
| WO | WO 98/21219 | 5/1998 |

OTHER PUBLICATIONS

Brandner et al., "Drying Oils from Sorbitol and Linseed Fatty Acids", *Industrial and Engineering Chemistry*, Sep. 1945, vol. 37, No. 9, pp. 809-812.

\* cited by examiner

METHOD FOR THE DIRECT ESTERIFICATION OF SORBITOL WITH FATTY ACIDS

This application is a continuation of U.S. Ser. No. 09/687,908 filed Oct. 12, 2000 now abandoned which claims the benefit of U.S. Ser. No. 60/159,563 filed Oct. 15, 1999.

BACKGROUND OF THE INVENTION

I. Field of the Invention

The present invention relates to a process for the production of sorbitol fatty acid esters through direct esterification. More specifically, the direct esterification process of the present invention is directed to the production of mixtures of sorbitol fatty acid esters with a degree of hydroxyl substitution ranging from about 3 to about 5.5 fatty acid ester groups, which are useful as low calorie fat substitutes.

II. Description of the Prior Art

Continued concern with health problems such as obesity and arteriosclerosis, which are associated with a diet high in fat content, has led to new formulations of normally high-caloric fat-containing foods. These formulations are often referred to as "diet," "lite" and "low calorie" and are made by replacing the normally present fat with fat substitutes, thereby reducing the fat content. It is generally known that certain sorbitol fatty acid esters and polyesters can be used as such fat substitutes.

Sorbitol fatty acid esters may be prepared by a variety of methods. These methods include transesterification of sorbitol with methyl, ethyl or glycerol fatty acid esters (U.S. Pat. Nos. 5,458,910 and 5,612,080), enzyme catalyzed direct esterification of sorbitol with fatty acids (U.S. Pat. No. 4,614,718), and acylation of sorbitol with a fatty acid chloride or anhydride.

Depending on the method by which the sorbitol fatty acid ester is made, it contains varying degrees of hydroxyl substitution and varying proportions of sorbitol anhydride esters. For example, when esterification is carried out by acylation of sorbitol with a fatty acid chloride, the product generally contains very little or no sorbitol anhydride esters. In contrast, transesterification of sorbitol with fatty acid methyl esters under basic conditions can result in a product in which about 15–20% of the sorbitol fatty acid esters are esters of sorbitol anhydrides. Additionally, depending on the method of production, the sorbitol fatty acid ester product can contain varying degrees of color. Organic solvents and bleaching agents may be required to obtain acceptably low color levels.

It is also generally known that fatty acid mono-and diesters of sorbitan and sorbide, useful as emulsifying agents, can be produced by direct, base-catalyzed reaction of sorbitol with fatty acids at elevated temperatures. Such processes are disclosed, for example, in U.S. Pat. No. 2,322,820 to Brown.

Previous methods for preparing mixtures of sorbitol fatty acid esters and sorbitol anhydride fatty acid esters with sufficiently low color values, such as are shown in U.S. Pat. Nos. 5,458,910 and 5,612,080, have involved a transesterification process comprising heating a mixture of sorbitol, an alkali metal fatty acid soap, an excess of a costly fatty acid alkyl ester, and a basic catalyst. Such processes necessarily required the use of organic solvents and bleaching agents in order to obtain acceptable product purity and color. However, use of such solvents and bleaching agents are greatly limited by environmental and governmental concerns.

It is accordingly an object of the present invention to develop a method for producing mixtures of sorbitol fatty acid esters with specified degrees of hydroxyl substitution and sufficiently low color values to enable their use as low calorie fat substitutes, without the need for organic solvents and bleaching agents, thus substantially removing these potential regulatory barriers. The present invention has the additional advantages of being more cost effective and simpler than previously known methods. Cost savings and process simplicity are realized largely through a significant reduction in the number of processing steps and the substantial elimination of the use of organic solvents.

SUMMARY OF THE INVENTION

When using sorbitol fatty acid esters as low calorie fat substitutes, the degree of hydroxyl substitution and the color of the product are often important properties. It is also advantageous to have a production process which is free of bleaching agents and regulated organic solvents such as methanol, hexane, or heptane-type solvents.

The present invention addresses the foregoing objects by providing a general method for the production of mixtures of sorbitol fatty acid esters and sorbitol anhydride fatty acid esters using relatively inexpensive free fatty acids which comprises the step of the direct esterification of sorbitol with free fatty acids, optionally in the presence of an esterification catalyst.

Therefore, the present invention relates to processes for the direct esterification of sorbitol with fatty acids. In particular, the process results in a product with a low color value and a degree of hydroxyl substitution ranging from about 3 to about 5.5. Additionally, the process may advantageously be carried out in the absence of organic solvents and bleaching agents.

In another embodiment, the present invention is directed to methods for producing mixtures of sorbitol fatty acid esters useful as low calorie fat substitutes through a direct esterification process.

In yet another embodiment, the present invention is directed to mixtures of sorbitol fatty acid esters and sorbitol fatty acid anhydride esters produced by the above direct esterification process which are useful as low calorie fat substitutes,

DETAILED DESCRIPTION OF THE INVENTION

Figure 1:
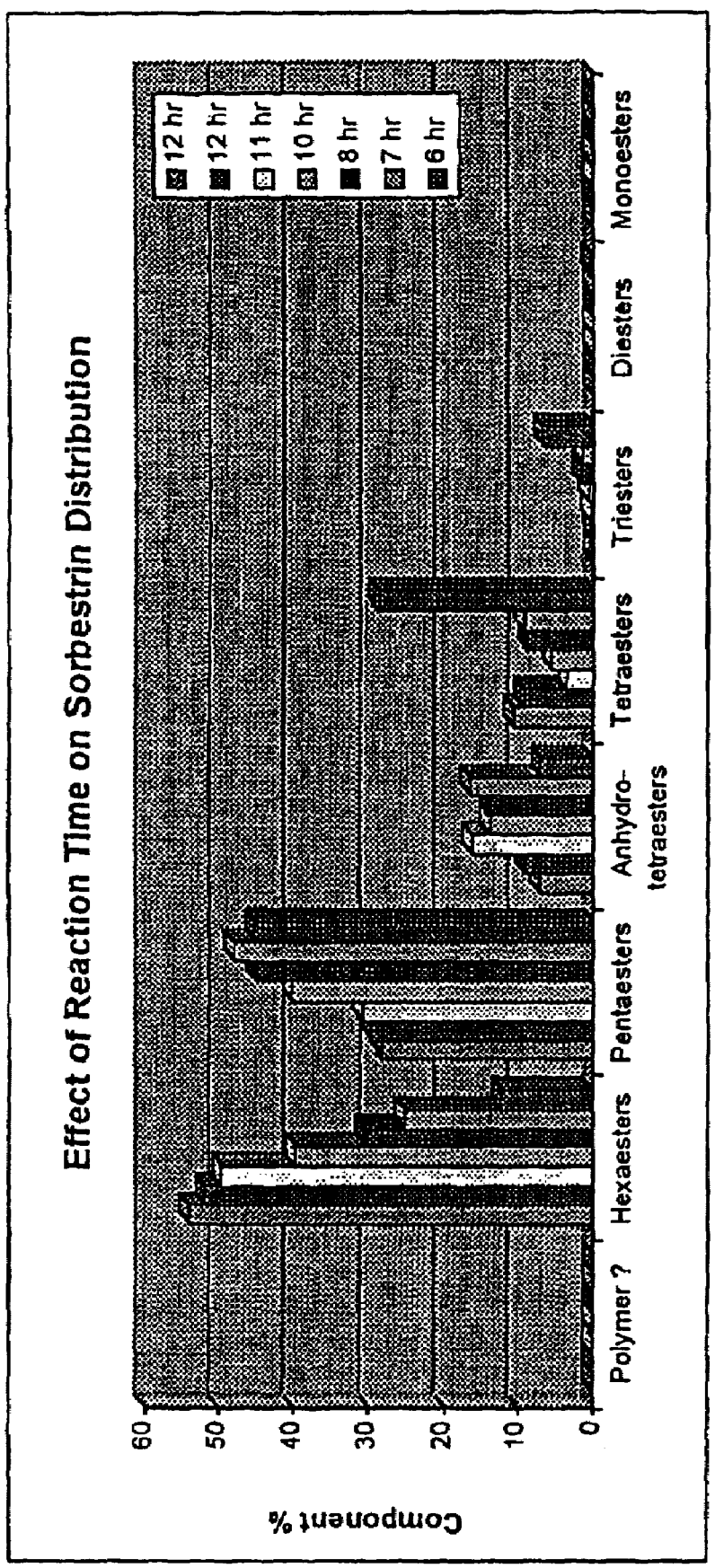
FIG. 1 - The bargraph shows the composition or the reaction product as a function of time. As reaction time increases, the average degree of substitution increases as does the levels of hexa-esters. Also note that the level of anhydro tetra-esters appears to go through a maximu as reaction time proceeds.

Sorbitol is a six-carbon sugar alcohol which contains six hydroxyl groups available for esterification. The monoanhydride forms of sorbitol contain four hydroxyl groups available for esterification. In the present invention, sorbitol is directly esterified with free fatty acids. Fatty acids are saturated or unsaturated carboxylic acids with hydrocarbon chains of from 2 to 22 carbon atoms. What is intended by the term free fatty acids is that the fatty acids are present in a form which has at least one free carboxylate group. In the esterified product mixture of the present invention, sorbitol ester species from triesters to hexaesters are present in significant amounts, with the average degree of hydroxyl substitution ranging from about 3 to about 5.5. In some embodiments, triesters and tetraesters of sorbitol anhydrides are also present in significant amounts. As an example, by an average degree of hydroxyl substitution of about 5, what is meant is that the weighted average of the degree of hydroxyl substitution of the total mixture of the sorbitol fatty acid ester species based on the weight of each individual ester species, as determined by High Performance Liquid Chromatography (HPLC), is about 5.

When used as a low calorie fat substitute, the sorbitol fatty acid esters of the present invention show advantages over the highly esterified polyol polyesters of the prior art. By virtue of their partial esterification, the sorbitol esters are partially hydrolyzed by mammalian intestinal lipases. While it is not intended that the invention be bound by theory, it is believed that non-metabolizable fat substitutes, such as the highly esterified polyol polyesters, hinder absorption of fat-soluble vitamins and other lipophilic nutrients by partitioning them (i.e., extracting them) into the oil phase of the intestinal contents, and that this process is greatly diminished in the partially hydrolyzed sorbitol esters. It is further believed that undesirable physiological side effects are minimized by the partially hydrolyzed esters because their surfactant properties facilitate emulsification within the gastrointestinal tract.

In addition to a controlled average degree of hydroxyl substitution, low product color levels should be obtained in order for the sorbitol fatty acid ester mixtures of the present invention to be useful as low calorie fat substitutes. Acceptable final product color levels for such a use are color levels below about 5, and preferably below about 1.5 on the Lovibond red scale. One influential factor with regard to color formation is the purity of the starting free fatty acids. Color development in the product is monitored using the Lovibond red scale and the "Wesson" 5.25 inch column with the AOCS-Tintometer Color Scale (AOCS Official Method Cc 13b-45).

As previously mentioned, the purity of the free fatty acids (FFAs) used in the esterification reaction may influence final product color. The FFAs should be essentially free of oxidative degradation products. Essentially free of oxidative degradation products means that there are insufficient amounts of impurities to cause unacceptable discoloration of the final product sorbitol fatty acid ester mixtures. FFAs are inherently less oxidatively stable than their corresponding fatty acid methyl esters and are chemically sensitive to oxidative degradation processes. Therefore, the FFAs should preferably be maintained in a substantially oxygen-free environment through various methods, such as through a constant nitrogen sparge. Additionally, the FFAs should advantageously be monitored for oxidative degradation products throughout processing and should be purified to remove any such degradation products.

Examples of useful FFAs include acetic, propionic, butyric, caprylic, caproic, capric, lauric, myristic, pelargonic, myristoleic, palmitic, palmitoleic, stearic, oleic, ricinoleic, undecanoic, linoleic, linolenic, eleostearic, elaidic, arachidic, arachidonic, behenic and erucic acids. Mixtures or blends of FFAs may also be used, such as those obtained from non-hydrogenated, partially hydrogenated, or hydrogenated soybean, safflower, sunflower, cocoa butter, cohune oat, tucum ucuhuba, sesame, peanut, corn, olive, rice bran, canola, babassu nut, coconut, palm kernel, shea nut, cottonseed, rapeseed, and palm oils; or butterfat, tallow or lard. FFAs useful in the present invention are typically derived from natural fat or oil, with a preferred form being derived from high-oleic sunflower oil.

The oxidative breakdown pathways of naturally occurring fats and oils are widely reported. Oxidative degradation products are easily detected in FFA blends using the peroxide test. Determination of peroxide values involve a wet chemical iodometric assay to elucidate the extent of formation of hydroperoxides, the precursors to oxidative degradation. However, as oxidation proceeds and susceptible fatty acids begin to degrade, the level of peroxides will eventually decrease. Because of this, peroxide values alone may, in some circumstances, give inaccurate results. As a further assurance of purity, one of the various carbonyl-detecting methods, such as the thiobarbituric acid or p-anisidine calorimetric assay, could also be employed.

On the whole, the oxidation breakdown products are shorter chain and chemically more volatile than the fatty acids from which they came. Therefore, vacuum distillation purification will remove most of the previously formed degradation products. The addition of adsorbents such as clays and activated carbon can be an effective means for removing the typically more polar degradation products such as aldehydes and ketones.

Additionally, adsorbents can be added to the esterification reaction mixture to control and minimize color formation. In the oil processing industry, it is common to employ activated carbons and clays to reduce color bodies in edible oils. These solids typically act by physically binding polar contaminants. In the present invention, small amounts of adsorbents can advantageously control the formation of hydroperoxides. Preferably, the use of adsorbents can be minimized through ensuring that the FFAs are essentially free of oxidative degradation products. Adsorbents useful in the current invention include clays and activated carbon.

In the present invention, sorbitol is esterified on an average of about 3 to about 5.5 of the hydroxyl groups with free fatty acids containing from about 2 to about 22 carbon atoms. In a preferred embodiment of the invention, an average of about 4 to about 5.5 hydroxyl groups are esterified and, most preferably an average of about 4 to about 5 hydroxyl groups are esterified. The degree of hydroxyl substitution is related to the reaction temperature and reaction time. Additional factors which may affect the degree of hydroxyl substitution, anhydride levels, reaction completion, and color formation include: the exclusion of air and water from the reaction, the concentrations of reactants and soap catalyst, the use of vacuum, and the use of adsorbents.

As the temperature of the reaction is increased, the rate of reaction also increases. The reaction is driven forward to more complete hydroxyl substitutions resulting in a higher proportion of hexaesters and lower proportions of mono, di, and triesters at higher temperatures. Overall degree of hydroxyl substitution and proper ester distributions can be controlled to some extent by adjusting (i.e. shortening) the reaction time as temperature is increased. Preferably, the temperature is controlled in a range of from about 170° C. to about 260° C., and more preferably between about 170° C. and about 190° C.

The effect of increasing reaction time is to drive the reaction towards more complete hydroxyl substitution. If the reaction time is too long, the proportion of hexaesters approaches unacceptable levels. On the other hand, too short of a reaction time results in a product that is under-esterified. Also, the level of anhydro tetraesters appears to go through a maximum as reaction time increases. Preferable reaction times range from about one half hour to about 24 hours, and more preferably, about 2 to about 8 hours.

The process of the present invention is preferably performed at atmospheric or sub-atmospheric pressures. The practice of using vacuum to drive the reaction towards more complete hydroxyl substitution has processing ramifications. For instance, the rate of reaction is significantly increased, but the level of hexa-substitution and anhydride ester production is enhanced. In addition, since the reaction is sensitive to color formation in the presence of oxygen, essentially no air leakage into the reactor can be tolerated.

In general, as the ratio of FFA to sorbitol in the reaction mixture increases, the esterification reaction is driven towards more complete hydroxyl substitutions. The molar ratio of FFA to sorbitol should be sufficient to affect the desired degree of hydroxyl substitution. In particular, the molar ratio of FFA to sorbitol is preferably at least 5:1 to produce a sufficient degree of esterification. At ratios of greater than about 15:1, there is little advantage to be gained, with more time being necessary to remove the unreacted FFAs, A preferred molar ratio range is from about 6:1 to about 15:1, with a particularly preferred range being from about 7:1 to about 12:1.

The process of the present invention can be carried out under substantially non-catalyzed conditions, or alternatively, in the presence of an esterification catalyst. When an esterification catalyst is used, the catalyst can be an alkali metal soap, an alkaline earth metal soap, an inorganic acid, a carboxylic acid, a polycarboxylic acid, or a salt, oxide, or hydroxide of an alkali metal, an alkaline earth metal, a transition metal, aluminum, or zinc. Preferably, the esterification catalyst, if used, is an alkali metal soap catalyst.

When an alkali metal soap catalyst is used, the quantity of soap catalyst has a relatively minor effect on the degree of esterification and distribution of hydroxyl substitutions. As a practical matter, less soap formation results in easier workup of the reaction. Lower levels of soap catalyst lead to under-reaction, and higher levels of soap tend to result in the formation of intractable emulsions that can only be broken by centrifugation. The amount of soap catalyst should be sufficient to catalyze the reaction, A preferred range is from about 0.3 moles to about 1.5 moles of alkali metal soap catalyst per mole of sorbitol, and a particularly preferred range is from about 0.5 moles to about 1.0 moles of alkali metal soap catalyst per mole of sorbitol.

The soap catalyst can be formed in a preliminary reaction step comprising heating a mixture of free fatty acids and an alkali metal compound until a homogeneous soap catalyst is formed, and then combining the soap catalyst with the sorbitol to form the reaction mixture. Alternatively, the soap catalyst can be formed in situ by combining an alkali metal compound with free fatty acids and sorbitol in the reaction mixture. In either case, the alkali metal compound used to form the soap catalyst is preferably potassium hydroxide, potassium carbonate, sodium hydroxide, sodium carbonate, sodium bicarbonate, or mixtures thereof.

Also important to the overall reaction rate is the removal of water from the reaction mixture. The reaction is preferably performed under conditions essentially free from water. By essentially free from water, it is intended that water not be present in amounts great enough to inhibit formation of a product with an average degree of hydroxyl substitution of from about 3 to about 5.5. If water is allowed to build up in the early stages of the reaction, the reaction may not proceed properly and di-, tri-, and tetra-esters will predominate over penta- and hexaesters. Methods to control water levels include the use of a nitrogen sparge and the use of vacuum during the reaction.

In a preferred embodiment of this invention, unreacted free fatty acids are separated from the product in the reaction mixture at the end of the reaction using vacuum distillation, and are recycled to subsequent esterification reaction mixtures. The oxidative degradation products maybe removed form the unreacted free fatty acids separated from the reaction mixture prior to recycling. Recycle of the unreacted free fatty acids into subsequent esterifications improves the economics of the process of the present invention. A typical recycle path for the present invention involves blending about 50% recycled free fatty acids with about 50% fresh free fatty acids, although many variations on this ratio are possible. Utilizing multiple recycles was not observed to have any significant effect on the final product in terms of ester distribution or free fatty acid composition. Additionally, free fatty acid ratios at all stages during the process are generally in close agreement with one another. As previously noted, attention must be given to the purity of the free fatty acids being recycled.

Further, because the reactants are dissolved in the excess free fatty acids, there is no need to use organic solvents to solubilize the reactants. The simpler process of the present invention therefore eliminates the need for organic solvents and bleaching agents, and also eliminates problems associated with emulsion breakage during processing.

The invention having been described in general terms, reference is now made to specific examples, it being understood that these examples are not meant to limit the present invention, the scope of which is to be determined by the appended claims.

EXAMPLE 1

Laboratory Scale, 180° C.

1.0 Mole Potassium Hydroxide and 10 Moles Fatty Acids Per Mole Sorbitol

A mixture of 60 grams (212 millimoles) of oleic acid and 1.2 grams (21.3 millimoles) of potassium hydroxide pellets was heated with stirring to 125° C. until almost homogeneous, and 3.88 grams (21.3 millimoles) of powdered sorbitol was added. The pressure was reduced to about 30 mm Hg, stirring was continued for 1 hour, the temperature was increased to 170–180° C., and stirring was continued for about 16 hours. By analysis, the product contained 20.1% oleic acid, 0.1% sorbitol dioleate, 1.5% sorbitol trioleate, 8.1% sorbitol tetraoleate, 7.6% sorbitol anhydride tetraoleate, 32.6% sorbitol pentaoleate, and 30.0% sorbitol hexaoleate. The average degree of hydroxyl substitution of sorbitol polyoleates was 5.0.

EXAMPLE 2

Laboratory Scale, 200° C.

1.0 Mole Potassium Hydroxide and 10 Moles Fatty Acids Per Mole Sorbitol

A mixture of 30 grams (106 millimoles) of oleic acid and 0.6 gram (10.6 millimoles) of powdered potassium hydroxide was heated under reduced pressure (approximately 30 mm Hg), with stirring, to 145° C. until homogeneous, and 1.94 grams (10.6 millimoles) of powdered sorbitol was added, The temperature was increased to 200° C., and stirring was continued for 4.3 hours. By analysis, the product contained 23.3% oleic acid, 0.3% sorbitol dioleate, 1.8% sorbitol trioleate, 5.6% sorbitol tetraoleate, 23.0% sorbitol anhydride tetraoleate, 25.3% sorbitol pentaoleate, and 20.7% sorbitol hexaoleate. The average degree of hydroxyl substitution of sorbitol polyoleates was 4.7.

EXAMPLE 3

Laboratory Scale, 200° C.

0.1 Mole Potassium Hydroxide and 5.5 Moles Fatty Acids Per Mole Sorbitol

A mixture of 16.4 grams (58.1 millimoles) of oleic acid and 0.06 gram (1.1 millimole) of powdered potassium hydroxide was heated with stirring to 100° C. until homogeneous, and 1.94 grams (10.6 millimoles) of powdered sorbitol was added. The pressure was reduced to about 30 mm Hg, the temperature was increased to 150° C., stirring was continued for 1 hour, the temperature was increased to 200° C., and stirring was continued for 6.8 hours. By analysis, the product contained no detectable oleic acid, 0.3% sorbitol dioleate, 7.4% sorbitol trioleate, 14.0% sorbitol tetraoleate, 15.4% sorbitol anhydride tetraoleate, 36.5% sorbitol pentaoleate, and 26.4% sorbitol hexaoleate. The average degree of hydroxyl substitution of sorbitol polyoleates was 4.6.

EXAMPLE 4

Laboratory Scale, 180° C.

1.0 Mole Potassium Hydroxide and 10 Moles Fatty Acids Per Mole Sorbitol

A mixture of 15.0 grams (53 millimoles) of fatty acids derived from Trisun 80 high-oleic acid sunflower oil (SVO Enterprises) and 0.3 gram (5.3 millimoles) of powdered potassium hydroxide was stirred under vacuum (approximately 30 mm Hg) at 130° C. until homogeneous, and 0.97 gram (5.3 millimoles) of powdered sorbitol was added. The temperature was increased to 180° C. and stirring was continued for 6 hours. By analysis, the product contained 26.5% fatty acids, a trace of sorbitol diesters, 3.1% sorbitol triesters, 12.5% sorbitol tetraesters, 14.7% sorbitol anhydride tetraesters, 34.5% sorbitol pentaesters, and 8.6% sorbitol hexaesters. The average degree of hydroxyl substitution was 4.6.

EXAMPLE 5

Laboratory Scale, 180° C.

1.5 Mole Potassium Hydroxide and 8 Moles Fatty Acids Per Mole Sorbitol

A mixture of 23.9 grams (84.6 millimoles) of oleic acid and 0.9 gram (15.9 millimoles) of powdered potassium hydroxide was stirred under vacuum (approximately 30 mm Hg) at 120–150° C. until homogeneous, and 1.94 grams (10.6 millimoles) of powdered sorbitol was added. The temperature was increased to 180° C. and stirring was continued for 4.7 hours. By analysis, the product contained 22.5% fatty acids, 2.0% sorbitol dioleate, 18.0% sorbitol trioleate, 26.1% sorbitol tetraoleate, 8.8% sorbitol anhydride tetraoleate, 20.6% sorbitol pentaoleate, and 2.0% sorbitol hexaoleate. The average degree of hydroxyl substitution of sorbitol polyoleates was 3.9.

EXAMPLE 6

Laboratory Scale, 180° C.

0.8 Mole Potassium Hydroxide and 8 Moles Fatty Acids Per Mole Sorbitol

With stirring at atmospheric pressure under a nitrogen atmosphere, a mixture of 60.79 grams (215.2 millimoles) of fatty acids derived from Trisun 80 high-oleic acid sunflower oil (SVO Enterprises), 1.23 gram (21.9 millimoles) of powdered potassium hydroxide, and 4.90 grams (26.9 millimoles) of powdered sorbitol was heated to 180° C. and held at this temperature for 6 hours. During heating and reaction, a nitrogen flow through the reaction flask of approximately 500 milliliters per minute was maintained to remove water formed by the esterification reaction. By analysis of samples removed during the reaction, the reaction mixture had the following compositions:

After 4 hours at 180° C., the reaction mixture contained 41.1% fatty acids, the distribution of sorbitol esters, by weight, was 0.4% diesters, 10.4% triesters, 28.0% tetraesters, 14.1% anhydride tetraesters, 40.0% pentaesters, and 7.1% hexaesters, and the average degree of hydroxyl substitution was 4.30.

After 5 hours at 180° C., the reaction mixture contained 39.9% fatty acids, the distribution of sorbitol esters, by weight, was 0.0% diesters, 5.1% triesters, 17.7% tetraesters, 16.9% anhydride tetraesters, 46.3% pentaesters, and 14.0% hexaesters, and the average degree of hydroxyl substitution was 4.57.

After 6 hours at 180° C., the reaction mixture contained 38.8% fatty acids, the distribution of sorbitol esters, by weight, was 0.0% diesters, 3.0% triesters, 10.9% tetraesters, 18.9% anhydride tetraesters, 46.0% pentaesters, and 21.1% hexaesters, and the average degree of hydroxyl substitution was 4.74.

EXAMPLE 7

Laboratory Scale, 180° C.

1.0 Mole Potassium Hydroxide, 0.33 Mole Potassium Carbonate, and 8 Moles Fatty Acids Per Mole Sorbitol With stirring at atmospheric pressure under a nitrogen atmosphere, a mixture of 60.79 grams (215.2 millimoles) of fatty acids derived from Trisun 80 high-oleic acid sunflower oil (SVO Enterprises), 1.50 gram (26.7 millimoles) of powdered potassium hydroxide, 1.23 gram (8.9 millimoles) of powdered potassium carbonate, and 4.90 grams (26.9 millimoles) of powdered sorbitol was heated to 180° C. and held at this temperature for 6 hours. During heating and reaction, a nitrogen flow through the reaction flask of approximately 500 milliliters per minute was maintained to remove water formed by the esterification reaction. By analysis of samples removed during the reaction, the reaction mixture had the following compositions:

After 4 hours at 180° C., the reaction mixture contained 43.0% fatty acids, the distribution of sorbitol esters, by weight, was 3.2% diesters, 20.2% triesters, 32.4% tetraesters, 9.6% anhydride tetraesters, 29.8% pentaesters, and 4.8% hexaesters, and the average degree of hydroxyl substitution was 3.95.

After 5 hours at 180° C., the reaction mixture contained 37.8% fatty acids, the distribution of sorbitol esters, by weight, was 1.4% diesters, 14.6% triesters, 28.6% tetraesters, 11.8% anhydride tetraesters, 36.2% pentaesters, and 7,3% hexaesters, and the average degree of hydroxyl substitution was 4.17.

After 6 hours at 180° C., the reaction mixture contained 37.0% fatty acids, the distribution of sorbitol esters, by weight, was 0.1% diesters, 7.0% triesters, 21.6% tetraesters, 13.7% anhydride tetraesters, 46.0% pentaesters, and 11.8% hexaesters, and the average degree of hydroxyl substitution was 4.50.

EXAMPLE 8

Laboratory Scale, 180° C.

0.4 Mole Potassium Carbonate and 8 Moles Fatty Acids Per Mole Sorbitol

With stirring at atmospheric pressure under a nitrogen atmosphere, a mixture of 60.80 grams (215.2 millimoles) of fatty acids derived from Trisun 80 high-oleic acid sunflower oil (SVO Enterprises), 1.48 gram (10.7 millimoles) of powdered potassium carbonate, and 4.90 grams (26.9 millimoles) of powdered sorbitol was heated to 180° C. and held at this temperature for 6 hours. During heating and reaction, a nitrogen flow through the reaction flask of approximately 500 milliliters per minute was maintained to remove water formed by the esterification reaction. By analysis of samples removed during the reaction, the reaction mixture had the following compositions:

After 4 hours at 180° C., the reaction mixture contained 42.1% fatty acids, the distribution of sorbitol esters, by weight, was 7.8% triesters, 20.8% tetraesters, 20.2% anhydride tetraesters, 42.2% pentaesters, and 9.0% hexaesters, and the average degree of hydroxyl substitution was 4.41.

After 5 hours at 180° C., the reaction mixture contained 38.6% fatty acids, the distribution of sorbitol esters, by weight, was 4.3% triesters, 12.7% tetraesters, 22.8% anhydride tetraesters, 44.8% pentaesters, and 15.3% hexaesters, and the average degree of hydroxyl substitution was 4.59.

After 6 hours at 180° C., the reaction mixture contained 37.1% fatty acids, the distribution of sorbitol esters, by weight, was 2.5% triesters, 9.2% tetraesters, 22.8% anhydride tetraesters, 42.4% pentaesters, and 23.1% hexaesters, and the average degree of hydroxyl substitution was 4.74.

EXAMPLE 9

Pilot Plant Scale, 179° C.

0.9 Mole Potassium Hydroxide and 8 Moles Fatty Acids Per Mole Sorbitol

With stirring under nitrogen at atmospheric pressure, a mixture of 28.7 kilograms (101.6 mols) of fatty acids derived from Trisun 80 high-oleic acid sunflower oil (SVO Enterprises), 0.71 kilogram of 90% potassium hydroxide (11.4 mols of KOH), and 2.32 kilograms (12.6 mols) of sorbitol was heated to 178–179° C. and held at this temperature for 5.2 hours with a nitrogen sparge to remove water formed by the esterification reaction. The mixture was cooled to about 120° C. and added, with stirring, to a mixture of 6.8 liters of water and 0.71 kilogram of concentrated sulfuric acid. The oil layer was separated, washed with 3.4 liters of water plus 0.35 kilogram of 16% sulfuric acid, washed with 3.4 liters of water plus 0.3 kilogram of 16% sulfuric acid, then washed with 3.4 liters of water, and residual water was removed by distillation at reduced pressure (1.5 mm Hg) for 0.5 hour at 81–87° C. Free fatty acids were removed by vacuum stripping at 4–19 mm Hg in a thin-film evaporator with a jacket temperature of 300° C. The product was 14.1 kilograms of oil containing 0.3% fatty acids, 0.4% sorbitol diesters, 6.2% sorbitol triesters, 16.6% sorbitol tetraesters, 19.1% sorbitol anhydride tetraesters, 37.0% sorbitol pentaesters, and 20.5% sorbitol hexaesters. The average degree of hydroxyl substitution was 4.6.

EXAMPLE 10

Pilot Plant Scale, 179° C.

0.9 Mole Potassium Hydroxide and 9 Moles Fatty Acids Per Mole Sorbitol

With stirring under nitrogen at atmospheric pressure, a mixture of 32.3 kilograms (114.0 mols) of fatty acids derived from Trisun 80 high-oleic acid sunflower oil (SVO Enterprises), 0.71 kilogram of 90% potassium hydroxide (11.4 mols of KOH), 2.32 kilograms (12.6 mols) of sorbitol, and 0.9 kilogram of Darco KBB activated carbon (American Norit) was heated to 175–183° C. and held at this temperature for 8 hours with a 0.5 cubic feet per minute nitrogen sparge to remove water formed by the esterification reaction. The mixture was cooled to about 140° C. and added, with stirring, to a mixture of 6.8 liters of water and 0.71 kilogram of concentrated sulfuric acid. The oil layer was separated, washed with 3.4 liters of water plus 0.2 kilogram of 16% sulfuric acid, washed with 3.4 liters of water plus 0.25 kilogram of 16% sulfuric acid, then washed with 3.4 liters of water, and residual water was removed by distillation at reduced pressure (approximately 1 mm Hg) for 1.3 hours at 85° C. The mixture was filtered with diatomaceous earth filteraid ("Super-Cel"), and free fatty acids were removed by vacuum stripping at 5–6 mm Hg in a thin-film evaporator with a jacket temperature of 298° C. The product was 9.0 kilograms of yellow oil containing 0.1% fatty acids, 0.1% sorbitol diesters, 2.7% sorbitol triesters, 13.7% sorbitol tetraesters, 9.7% sorbitol anhydride tetraesters, 35.8% sorbitol pentaesters, and 37.9% sorbitol hexaesters. The average degree of hydroxyl substitution was 5.0 and the final color value was 1.0 on the Lovibond red scale.

EXAMPLE 11

Pilot Plant Scale, 177° C.

0.9 Mole Potassium Hydroxide and 8 Moles Fatty Acids Per Mole Sorbitol

With stirring under nitrogen at atmospheric pressure, a mixture of 57.4 kilograms (202.9 mols) of fatty acids derived from Trisun 80 high-oleic acid sunflower oil (SVO Enterprises), 1.40 kilograms of 90% potassium hydroxide (22.5 mols of KOH), 4.60 kilograms (25.0 mols) of sorbitol, and 0.34 kilogram of Darco KBB activated carbon (American Norit) was heated to 174–179° C. and held at this temperature for 6 hours, with a 0.5 cubic feet per minute nitrogen sparge to remove water formed by the esterification reaction. The mixture was cooled to about 130° C. and added, with stirring, to a mixture of 13.6 liters of water and 6.2 kilograms of 50% phosphoric acid. The oil layer was separated, washed twice with 6.8 liters of water plus 0.12 kilogram of 50% phosphoric acid, washed once with 6.8 liters of water, and residual water was removed by distillation at reduced pressure (200 mm Hg) for 1.3 hours at 70–80° C. The mixture was filtered with 0.14 kilogram of diatomaceous earth filteraid ("Super-Cel"), and free fatty acids were removed by vacuum stripping at 1–2 mm Hg in a thin-film evaporator with a jacket temperature of 298° C. The product was 30.6 kilograms of yellow oil containing 0.1% fatty acids, 0.2% sorbitol diesters, 6.7% sorbitol triesters, 20.4% sorbitol tetraesters, 10.8% sorbitol anhydride tetraesters, 38.4% sorbitol pentaesters, and 23.5% sorbitol hexaesters. The average degree of hydroxyl substitution was 4.6 and the final color value was 0.6 on the Lovibond red scale.

EXAMPLE 12

Pilot Plant Scale, 177° C.

0.5 Mole Potassium Hydroxide and 8 Moles Fatty Acids Per Mole Sorbitol

With stirring under nitrogen at atmospheric pressure, a mixture of 57.4 kilograms (202.4 mols) of fatty acids derived from Trisun 80 high-oleic acid sunflower oil (SVO Enterprises), 1.56 kilograms of 45% potassium hydroxide solution (12.5 mols of KOH), 4.64 kilograms (25.2 mols) of sorbitol, and 0.34 kilogram of Darco KBB activated carbon (American Norit) was heated to 175–178° C. and held at this temperature for 7.5 hours, with a 0.5 cubic feet per minute nitrogen sparge to remove water formed by the esterification reaction. The mixture was cooled to about 130° C. and added, with stirring, to a mixture of 13.6 liters of water and 0.78 kilogram of concentrated sulfuric acid. The oil layer was separated, washed twice with 6.8 liters of water plus 0.4 kilogram of 16% sulfuric acid, then washed once with 6.8 liters of water, and residual water was removed by distillation at reduced pressure (75–100 mm Hg) for 1.7 hours at 85–96° C. The mixture was filtered with 0.12 kilogram of diatomaceous earth filteraid ("Super-Cel"), and free fatty acids were removed by vacuum stripping at 5–6 mm Hg in a thin-film evaporator with a jacket temperature of 298° C. The product was 30.5 kilograms of yellow oil containing 0.2% fatty acids, 0.1% sorbitol diesters, 3.7% sorbitol triesters, 17.0% sorbitol tetraesters, 9.8% sorbitol anhydride tetraesters, 39.9% sorbitol pentaesters, and 29.5% sorbitol hexaesters. The average degree of hydroxyl substitution was 4.8 and the final color value was 0.4 on the Lovibond red scale.

What is claimed is:

1. A process for preparing a mixture of sorbitol fatty acid esters and sorbitol anhydride fatty acid esters comprising the step of:
reacting a reaction mixture which is essentially free from water, comprising sorbitol and at least one free fatty acid, wherein the molar ratio of free fatty acid to sorbitol is at least 7:1, at a temperature and for a time sufficient to effect an average degree of sorbitol hydroxyl substitution of from about 3 to about 5.5 fatty acid groups per sorbitol molecule, thereby forming an esterified reaction product mixture comprising sorbitol fatty acid esters and sorbitol anhydride fatty acid esters.

2. The process of claim 1, wherein said reaction mixture further comprises an esterification catalyst.

3. The process of claim 2, wherein said esterification catalyst is selected from the group consisting of alkali metal soaps, alkaline earth metal soaps, inorganic acids, carboxylic acids, polycarboxylic acids, and salts, oxides and hydroxides of alkali metals, alkaline earth metals, transition metals, aluminum, and zinc.

4. The process of claim 2, wherein said esterification catalyst is an alkali metal soap.

5. The process of claim 1, wherein said average degree of sorbitol hydroxyl substitution is about 4.0 to about 5.5 fatty acid groups per sorbitol molecule.

6. The process of claim 1, wherein the molar ratio of free fatty acid to sorbitol is from about 7:1 to about 15:1.

7. The process of claim 1, wherein the molar ratio of free fatty acid to sorbitol is from about 7:1 to about 12:1.

8. The process of claim 1, wherein said reaction mixture is reacted at a temperature of from about 170 to about 260° C.

9. The process of claim 1, wherein said reaction mixture is reacted at a temperature of from about 170 to about 190° C.

10. The process of claim 1, wherein said reaction mixture is reacted for a time of from about one half to about 24 hours.

11. The process of claim 1, wherein said reaction mixture is reacted for a time of from about 2 to about 8 hours.

12. The process of claim 4, wherein said alkali metal soap catalyst is formed in situ from an alkali metal compound and the at least one free fatty acid present in said reaction mixture.

13. The process of claim 4, wherein said alkali metal soap catalyst is formed prior to said reacting step in a preliminary step comprising heating a mixture of an alkali metal compound and at least one free fatty acid.

14. The process of claim 12, wherein said alkali metal compound is selected from the group consisting of potassium hydroxide, potassium carbonate, sodium hydroxide, sodium carbonate, sodium bicarbonate, and mixtures thereof.

15. The process of claim 13, wherein said alkali metal compound is selected from the group consisting of potassium hydroxide, potassium carbonate, sodium hydroxide, sodium carbonate, sodium bicarbonate, and mixtures thereof.

16. The process of claim 4, wherein said alkali metal soap catalyst is present in an amount ranging from about 0.3 mole to about 1.4 mole, per mole of sorbitol present in the reaction mixture.

17. The process of claim 1, wherein said at least one free fatty acid is selected from the group consisting of acetic, propionic, butyric, caproic, caprylic, pelargonic, capric, undecanoic, lauric, myristic, palmitic, oleic, elaidic, myristoleic, palmitoleic, ricinoleic, erucic, stearic, arachidic, behenic, linoleic, linolenic, eleostearic, arachidonic acids, and mixtures thereof.

18. The process of claim 1, wherein said at least one free fatty acid is obtained from non-hydrogenated, partially hydrogenated and hydrogenated oils selected from the group consisting of soybean oil, safflower oil, sunflower oil, sesame oil, peanut oil, corn oil, olive oil, rice bran oil, canola oil, rapeseed oil, shea nut oil, babassu nut oil, coconut oil, palm kernal oil, cottonseed oil, palm oil, cocoa butter, cohune oat, tacum ucuhuba, butterfat, tallow, lard, and mixtures thereof.

19. The process of claim 1, wherein said at least one free fatty acid is essentially free of oxidative degradation products.

20. The process of claim 1, wherein the reaction mixture further comprises an absorbent selected from the group consisting of activated carbon and clay.

21. The process of claim 1, further comprising the steps of:
   separating unreacted free fatty acid from said esterified reaction product,
   removing oxidative degradation products from the unreacted free fatty acid, and
   recycling the unreacted free fatty acid free of oxidative degradation products to the reaction mixture.

22. The process of claim 21, wherein vacuum distillation is used to remove the oxidative degradation products from the unreacted free fatty acid.

23. The process of claim 19, wherein the reaction products exhibit a Lovibond red scale color of about 5 or less.

24. The process of claim 19, wherein the reaction products exhibit a Lovibond red scale color below about 1.5.

* * * * *